United States Patent
Souta et al.

(10) Patent No.: US 7,974,670 B2
(45) Date of Patent: Jul. 5, 2011

(54) METHOD OF MEASURING SUPERFICIAL CHEMICAL SPECIES AND APPARATUS FOR MEASURING THE SAME

(75) Inventors: Takayuki Souta, Tokyo (JP); Katsuo Aizawa, Tokyo (JP); Atsushi Nakamura, Tokyo (JP); Satoshi Kageyama, Tokyo (JP); Shinya Ohtsubo, Tokyo (JP); Fumihiko Ichikawa, Yotsukaido (JP)

(73) Assignee: Waseda University, Tokyo (JP)

( * ) Notice: Subject to any disclaimer, the term of this patent is extended or adjusted under 35 U.S.C. 154(b) by 1287 days.

(21) Appl. No.: 10/590,407

(22) PCT Filed: Feb. 22, 2005

(86) PCT No.: PCT/JP2005/002821
§ 371 (c)(1),
(2), (4) Date: Aug. 23, 2006

(87) PCT Pub. No.: WO2005/079661
PCT Pub. Date: Sep. 1, 2005

(65) Prior Publication Data
US 2007/0173725 A1    Jul. 26, 2007

(30) Foreign Application Priority Data
Feb. 24, 2004 (JP) .................... 2004-047987

(51) Int. Cl.
*A61B 5/1455* (2006.01)
(52) U.S. Cl. .............. 600/323; 600/310; 600/476
(58) Field of Classification Search ................ 600/476, 600/309–344
See application file for complete search history.

(56) References Cited

U.S. PATENT DOCUMENTS
5,596,992 A    1/1997   Haaland et al.
5,784,162 A    7/1998   Cabib et al.
(Continued)

FOREIGN PATENT DOCUMENTS
DE         19638839         3/1998
(Continued)

OTHER PUBLICATIONS
Ichikawa, Fumihiko, et al., "Kokando Real Time Bunko Gazo System no Shisaku", Nihon Bunko Gakkai Koen Yoshishu, 2001, vol. 2001, Shuki, pp. 18-19.
(Continued)

*Primary Examiner* — Eric F Winakur
*Assistant Examiner* — Marjan Fardanesh
(74) *Attorney, Agent, or Firm* — McDermott Will & Emery LLP

(57) ABSTRACT

A method of processing skin surface observation measuring data which is able to address various sicknesses and reduce an error in sickness detection, and a measuring apparatus requiring no filter. The measuring apparatus an irradiator applying a white light to a biological surface as a sample, a detector detecting the spectra of the white light reflected off a plurality of positions on the biological surface, a plotter plotting the absorbances of the above spectra to a light spectrum multi-dimensional space, an analyzer subjecting data in the spectrum multi-dimension space obtained from the plurality of positions to multivariate analysis to determine the eigenvectors of at least first, second and third principal components, and a display projecting data at respective positions in respective eigenvector directions to display their magnitudes on a two-dimension display screen on a gray scale or in colors corresponding to the magnitudes; and a measuring method by the apparatus.

9 Claims, 12 Drawing Sheets

U.S. PATENT DOCUMENTS

| | | |
|---|---|---|
| 6,587,702 B1 * | 7/2003 | Ruchti et al. .................. 600/310 |
| 2003/0032064 A1 * | 2/2003 | Soller et al. .................... 435/7.1 |
| 2004/0243198 A1 * | 12/2004 | Heacock et al. ................ 607/89 |

FOREIGN PATENT DOCUMENTS

| | | |
|---|---|---|
| JP | H09-47432 | 2/1997 |
| JP | 10-85222 A | 4/1998 |
| JP | 10-90062 A | 4/1998 |
| JP | H11-332834 | 12/1999 |
| JP | 2000-356552 | 12/2000 |
| JP | 2001-104237 | 4/2001 |
| JP | 2003-144393 | 5/2003 |
| JP | 2003-339648 | 12/2003 |
| WO | WO-9922640 | 5/1999 |
| WO | WO-0226152 | 4/2002 |
| WO | WO-03043492 | 5/2003 |
| WO | 03-094695 A2 | 11/2003 |
| WO | WO-2004012586 | 2/2004 |

OTHER PUBLICATIONS

Geladi et al., "A multivariate NIR study of skin alterations in diabetic patients as compared to control subjects", J. Near Infrared Spectrosc. 8, 217-227 (2000). XP-002534719.

* cited by examiner

Hemoglobin

Second Principal Component

Oxygenated Hemoglobin

Third Principal Component

Wavelength Band 500nm ~ 600nm

Hemoglobin

Second Principal Component

Reduced Hemoglobin

Third Principal Component

Wavelength Band 500nm ~ 850nm

Second Principal Component

Wavelength Band 500nm ~ 600nm

Third Principal Component

Wavelength Band 700nm ~ 780nm

Score vs Melanin Concentration (mg/ml)

Second Principal Component

Third Principal Component

Wavelength Band 500nm ~ 600nm

Wavelength Band 500nm ~ 800nm

Wavelength Band 700nm ~ 780nm

Hemoglobin

Second Principal Component

Wavelength Band 500nm ~ 800nm

Reduced Hemoglobin

Third Principal Component

Wavelength Band 500nm ~ 600nm

Skin Surface

Before Administration of Talaporfin

Shortly After Administration of Talaporfin

Forty Five Minutes

Seventy Minutes

After Photo Dynamic Therapy

Second Principal Component
Wavelength Band 600nm ~ 700nm 0.15
0.1
0.05
0
-0.05
-0.1

Skin Surface

Before Administration of Talaporfin

Shortly After Administration of Talaporfin

Forty Five Minutes

Seventy Minutes

After Photo Dynamic Therapy

Third Principal Component
Wavelength Band 500nm ~ 600nm

| Trial Subject | Age | 50% | 70% | 90% |
|---|---|---|---|---|
| A | 64 | 4.5 sec | 6 sec | 9 sec |
| T | 62 | 3.5 sec | 4.5 sec | 6 sec |
| I | 56 | 3 sec | 5 sec | 7 sec |
| N | 28 | 4 sec | 4.5 sec | 7 sec |
| K | 24 | 2 sec | 3 sec | 5.5 sec |

FIG.20

| Trial Subject | Age | 50% | 70% | 90% |
|---|---|---|---|---|
| A | 64 | 5.5 sec | 7 sec | 12 sec |
| T | 62 | 4 sec | 5 sec | 6.5 sec |
| I | 56 | 5 sec | 6 sec | 8 sec |
| N | 28 | 4 sec | 5 sec | 7 sec |
| K | 24 | 4 sec | 5 sec | 6.5 sec |

METHOD OF MEASURING SUPERFICIAL CHEMICAL SPECIES AND APPARATUS FOR MEASURING THE SAME

CROSS-REFERENCE TO PRIOR RELATED APPLICATIONS

This application is a U.S. National Phase Application under 35 U.S.C. §371 of International Application No. PCT/JP2005/002821 filed Feb. 22, 2005, which in turn claims priority to JP2004-047987 filed Feb. 24, 2004. The International Application was published in Japanese on Sep. 1, 2005 as WO 2005/079661 under PCT Article 21(2).

TECHNICAL FIELD

The present invention relates to a method of measuring a blood flow in a biological surface or the like by conducting a spectral analysis of a light reflected from the biological surface to which a white light is irradiated. The present invention also relates to an apparatus for measuring the same.

BACKGROUND OF THE INVENTION

Conventional diagnosis of skin cancer etc. has been made by pathological analysis, e.g., seeing the color of the skin, touching the skin by hand and/or taking a living tissue as a sample therefor. Observation by taking a living tissue sample, however, creates a painful burden to the patient, and can cause metastasis thereof if it is virulent cancer. Thus, it is not desirable to take a living tissue sample.

As a solution, a noninvasive test method has heretofore been proposed, wherein the color of the skin surface at respective positions is split so that a light of a wavelength specific to a predicted pathological change is detected through a plurality of filters, displaying the reflection intensity thereof as a two-dimensional image. An apparatus for measuring and displaying such spectroscopic images of colors are disclosed in Japanese Un-examined Patent Publication No. 2000-356552, for example.

The conventional measuring methods and apparatuses, however, have problems that there are many errors in detecting a pathological change since an image is obtained by choosing a wavelength characteristic of a specific color in accordance with an intended purpose, and then filtering the same; and that the measuring apparatuses become too complex since they use a plurality of filters.

SUMMARY OF THE INVENTION

An object of the present invention is to provide a method for processing skin surface observation measurement data that can solve the above-mentioned problem, and respond to various pathological changes with less detection errors thereof. It is another object of the present invention to provide a measuring apparatus used for that purpose that has a simple structure, eliminating the need for any filters.

A method of measuring a biological surface according to a first aspect of the invention which includes the steps of irradiating a white light to the biological surface as a sample; and detecting a spectrum of the white light reflected from two or more positions on said biological surface. Further steps include plotting an absorbance of said spectrum to a spectral multi-dimensional space of light; conducting a multivariate analysis of a data on said spectral multi-dimensional space obtained from said two or more positions to obtain eigenvectors of at least first, second and third principal components; and projecting the data of each position onto a direction of the eigenvector to measure at least one of the concentration of the superficial chemical species on said biological surface and a concentration difference therebetween, based on a magnitude of the component of said data with respect to the direction of said eigenvector.

Displaying each eigenvector to display a magnitude thereof on a gray scale or in colors according to the magnitude, on a two-dimensional screen.

According to the above measuring method, since all the spectra reflected from each position of the biological surface used as a sample are detected to allow them to undergo statistical data processing, no filter is needed. Further, since the condition of a biological surface is measured and displayed by comprehensive analysis of a wide range of data, it is effective to decrease errors in detecting pathological changes.

Further, since the multivariate analysis is conducted with a basic wavelength band of light used for data processing ranging from 500-600 nm and 500-850 nm, it is effective for observing, for example, diabetic peripheral vascular obstruction syndrome or the post-transplant condition of a transplanted skin, enabling errors in detecting pathological changes to be lessened.

Since the multivariate analysis is conducted with a basic wavelength band of light used for data processing ranging from 500-600 nm and 700-780 nm, not only a melanin amount in the skin such as a mole, but also a cancer hidden in the mole can be detected.

Specifically, as the multivariate analysis is conducted to calculate the score with respect to an eigenvector corresponding to melanin, melanin amount can be predicted using a calibration curve, thus enabling a patient to undergo treatment before pathological change occurs.

Still further, as the multivariate analysis is conducted with a basic wavelength band of light used for data processing ranging from 500-600 nm, 500-850 nm and 700-780 nm, it is effective for detecting a superficial cancer cell, for example.

Furthermore, since a light-sensitive substance is administered to a biological surface for treatment of a cancer, and the multivariate analysis is conducted with a basic wavelength band of light used for data processing ranging from 500 to 600 nm, 500 to 850 nm and 700 to 780 nm, further including a wavelength band specific to said light-sensitive substance, it is possible to observe the position of the cancer as well as the therapeutic effect by the light-sensitive substance having an absorption band in this wavelength band.

Still further, the multivariate analysis is conducted with a basic wavelength band of light used for data processing ranging from 700 nm or above. Since such light is eye-safe one, it is possible, for example, to observe a blood flow and a relative amount of oxygenated hemoglobin and reduced hemoglobin on retina at the back of the eye.

Moreover, since the multivariate analysis is conducted with a basic wavelength band of light used for data processing ranging from 500 to 600 nm, and 700 to 780 nm, to measure a moment-to-moment change of spectral information from subcutaneous peripheral blood vessels, it is possible to detect pathological changes such as hyperlipemia and abnormal glucose tolerance.

Also, the foregoing data measuring apparatus is the one that enables the implementation of the above-mentioned measuring method, eliminating the need for a filter which the conventional apparatuses would require, thus simplifying the structure of the apparatus.

Still moreover, according to the foregoing data measuring apparatus, the apparatus is combined with an optical fiber, and thus a white light irradiation part integral with a reflection condensing part is separable from a spectroscopic-analysis part. The apparatus structured as above enables the provision of an apparatus applicable to the inspection at the time of intraoral, craniotomy or abdominal operation, etc, as well as a measuring apparatus that enables easy inspection of a digestive organ, a respiratory organ and a wall surface of a blood vessel in combination with a conventional alimentary system endoscope, a respiratory system endoscope or a vascular catheter.

According to the present invention, there can be provided a measuring method that can respond to various pathological changes with less detection errors thereof. Further, the measuring apparatus therefor does not need any filter, thus simplifying the structure of the apparatus.

BRIEF DESCRIPTION OF THE DRAWINGS

FIG. 20 is a table showing the time taken for the score of the second principal component measured by the apparatus of FIG. 1 with a wavelength band from 500 nm to 850 nm to rise to 50%, 70% and 90%.

DETAILED DESCRIPTION OF THE INVENTION

Figure 1:
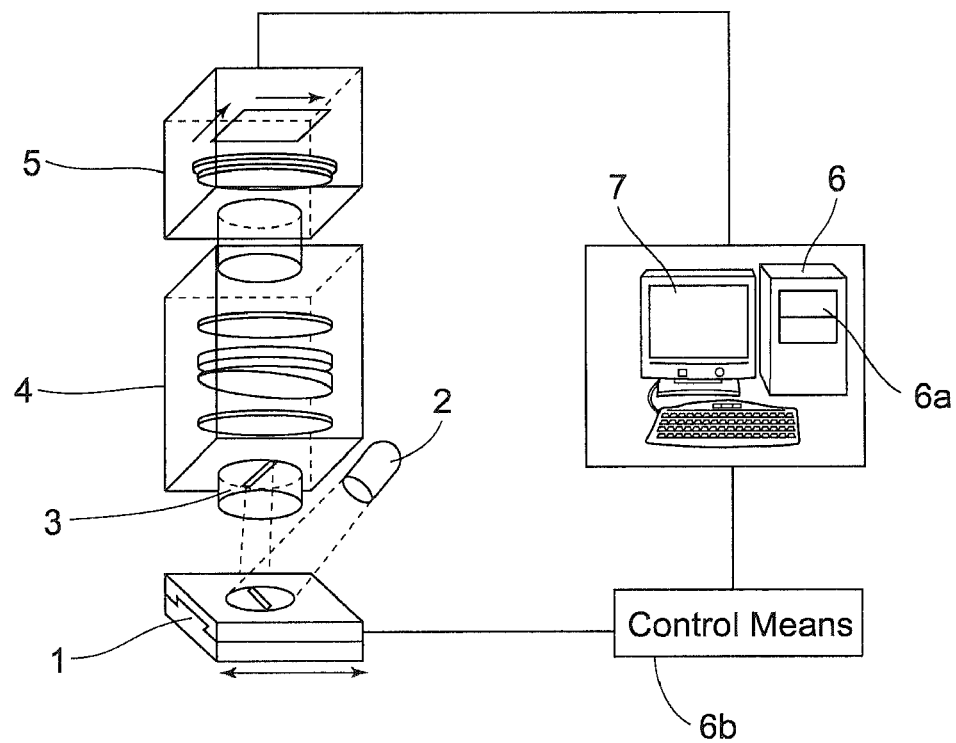
FIG. 1 is a schematic diagram showing a measuring apparatus in accordance with the present invention.

Next is a description of preferred embodiments of the present invention. First, a measuring apparatus of the present invention will be explained with reference to FIG. 1 and FIG. 2. In FIG. 1, numeral 1 designates a stage on which a sample S is placed, while numeral 2 designates a white light source. A spectroscope 4 provided with a slit 3 is provided above the stage 1.

The spectroscope 4 is an imaging spectroscope equipped with a transmission grating. The light reflected from one line of a sample is allowed to pass through the slit 3, and then separated (split) by the spectroscope 4 to thereby form an image on an acceptance surface of a CCD camera 5. In other words, X axis of the acceptance surface of the CCD camera 5 corresponds to a position of the sample on the one line, while the light is separated into a spectrum in the direction of Y axis thereof.

Figure 2:
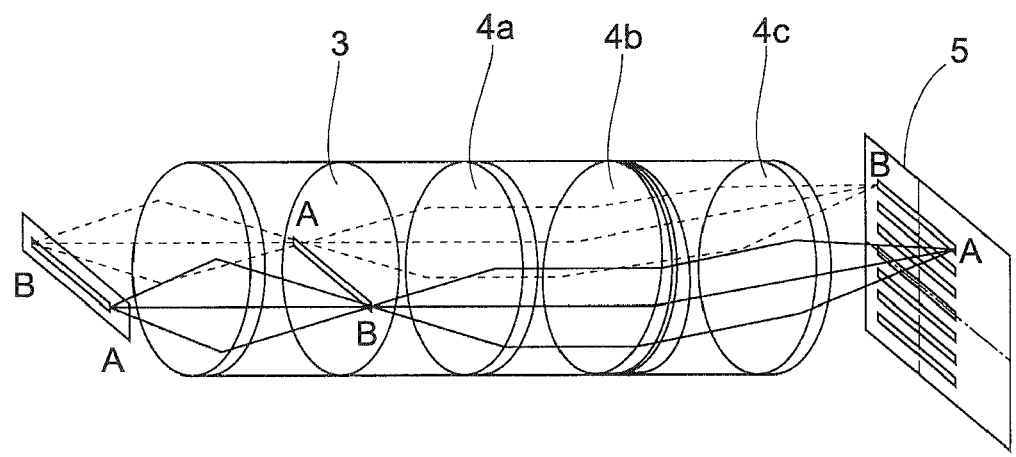
FIG. 2 is a schematic diagram showing the structure of a spectroscope mounted in the measuring apparatus of the present invention.

The structure of the spectroscope 4 is illustrated in detail in FIG. 2. The spectroscope 4 comprises the slit 3 composed of a slit body 3a and a lens 3b for focusing light. The spectroscope 4 further comprises two lenses 4a, 4c and a prism 4b of a transmission grating type provided therebetween. The camera 5 is equipped with a photo-multiplier 5a to raise sensitivity so that it can sense even a weak light.

Since the structure of the optical portion of this measuring apparatus is as described above, spectral data from one line of the sample S can be obtained on one frame of the CCD camera. The data are inputted into a data processing equipment 6. Then, the stage is moved a minute distance to thereby obtain subsequent one-line spectral data on a next frame of the CCD camera, which are then sent to the data processing equipment 6.

By repeating this operation, a spectral data of a two-dimensional field can be obtained. In reality, the data can be obtained by the CCD camera 5 synchronously with a substantially continuous movement of the stage 1 by a mechanism such as an adjusting means 7 for sweeping in a direction perpendicular to the one line of the surface of the sample, corresponding to the above-mentioned X axis.

Moreover, since the measuring apparatus is combined with an optical fiber, a white light irradiation part integral with a reflection condensing part is separated from a spectroscopic-analysis part. Thus, it is possible to measure a visceral condition observable via the optical fiber as well as a skin surface condition.

The apparatus structured as above is applicable to the inspection at the time of intraoral, craniotomy or abdominal operation, enabling easy inspection of a digestive organ, a respiratory organ and a wall surface of a blood vessel in combination with a conventional alimentary system endoscope, a respiratory system endoscope or a vascular catheter.

Next, a method of processing the data obtained as above is explained in detail. Whilst the size of a minute region of a sample to be detected is determined by the slit 3a and the magnification of the object lens 3b, the S/N ratio of the spectral data is improved by taking the average of the spectral data of four adjacent minute regions.

Thus, the spectral data obtained in each position is plotted to a spectral multi-dimensional space. For example, if the wavelength of the obtained data is 500 nm to 600 nm, it is divided by a minimum resolution of 5 nm, and then absorbance (in arbitral unit) at respective wavelengths are determined, thus plotting one point against one position in the 20-dimensional space divided thus way.

For example, assuming that the size of a sample is 0.01 square millimeter, and the minute region to be detected is 0.01 square millimeter, then the spectral data from 10,000 minute regions are obtained. For example, when the data of four minute regions are averaged for the purpose of improving a S/N ratio, then the number of the data finally obtained is 2,500. These 2,500 spectral data are plotted to the above-mentioned 20-dimensional spectral space.

Next, a direction where variance of the 2,500 points becomes the greatest in the 20-dimensional spectral space is determined as the first principal component, using, for example, the technique of multivariate analysis, such as principal component analysis (PCA), thus making that direction the eigenvector of the first principal component. Then, each plotting point is projected on a space orthogonal to the first eigenvector to determine the second principal component, thus making the same the eigenvector of the second principal component. In this way, the third to the nth principal components, and the third to the nth eigenvectors are determined according to the same procedure.

Thus, the eigenvectors of the first, second and third principal components are determined, respectively, while the aforesaid 2,500 plotted data are projected on each of the eigenvectors. In other words, the component in the direction of each eigenvector is determined. The magnitude of the component is called a score. The score in the direction of each eigenvector is plotted to each position of a sample on a gray scale or in colors according to the value of each score, thus displaying the same in a two-dimensional expression.

Figure 3:
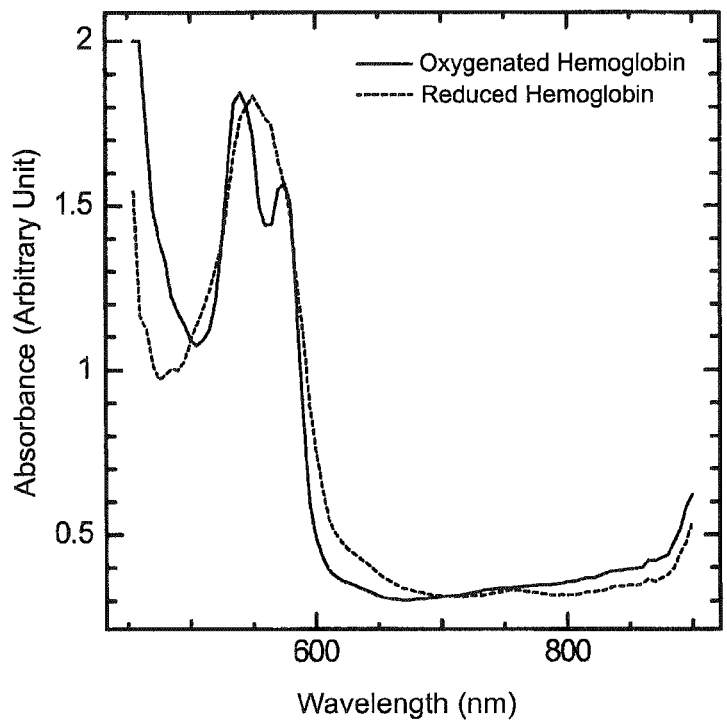
FIG. 3 is a graph showing spectral absorption characteristics of human blood.

FIG. 3 shows a spectral absorption characteristic of human blood. A horizontal axis denotes a wavelength of light while a vertical axis denotes absorbance (in arbitrary unit). In FIG. 3, one of the two graphs shows the absorption spectrum of oxygenated hemoglobin, while the other thereof shows the absorption spectrum of reduced hemoglobin.

The characteristic difference between the two absorption spectra lies in that there are two peaks in the absorption spectrum of oxygenated hemoglobin, while one peak in that of reduced hemoglobin with regard to the form of peak between 500 nm and 600 nm. Another difference is noted between 700 nm and 800 nm where the absorption spectrum of oxygenated hemoglobin is flat, while the absorption spectrum of reduced hemoglobin has one peak.

Figure 4:
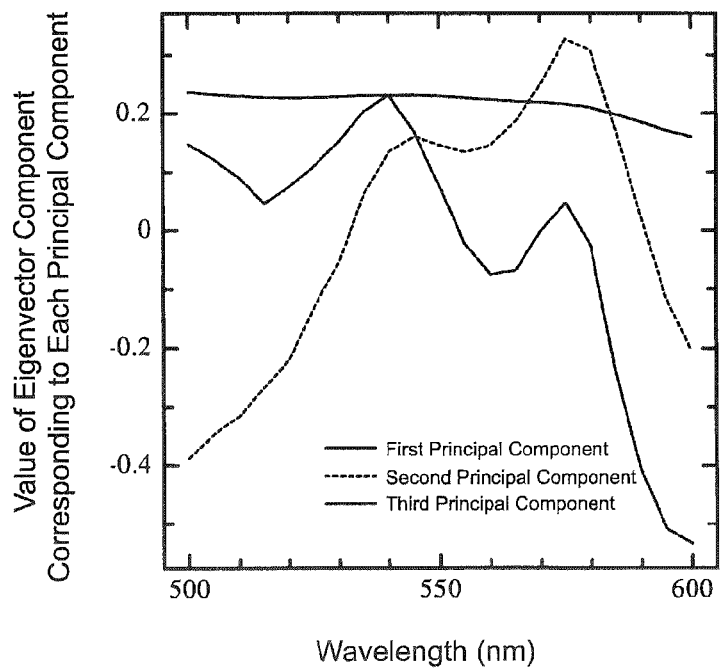
FIG. 4 is a graph showing components of eigenvectors corresponding to respective principal components calculated from the spectra from the normal skin.

In FIG. 4 showing a first embodiment, the value of each eigenvector component relative to a certain wavelength is shown when the normal skin as a sample is measured, using a wavelength band from 500 nm to 600 nm.

The eigenvector component corresponding to the first principal component shows a total average of the 2,500 spectrums. The eigenvector component corresponding to the second principal component shows a spectrum corresponding to the total amount of hemoglobin, and that of the third principal component shows a difference spectrum of the oxygenated hemoglobin spectrum and the reduced hemoglobin spectrum.

Figure 5A:
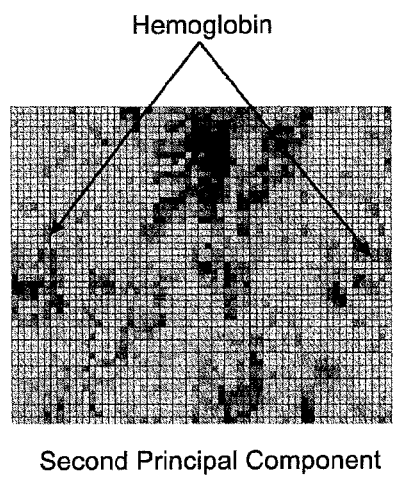
FIG. 5 is a two-dimensional representation of images of the score values from the normal skin measured by the apparatus of FIG. 1 with a wavelength band of from 500 nm to 600 nm according to the first embodiment of the invention.
Figure 5B:
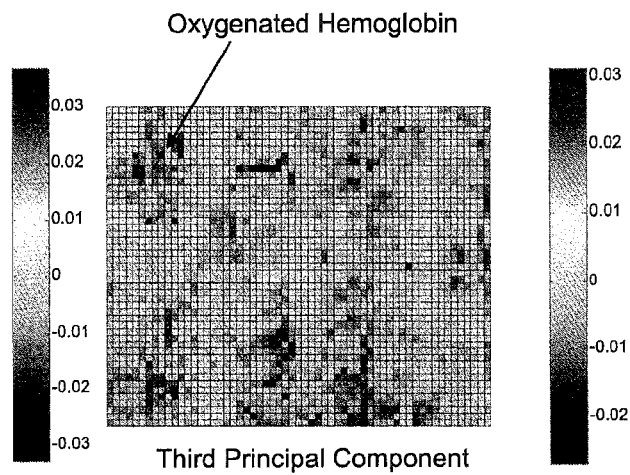

FIGS. 5(a) and 5(b) are each two-dimensional representation of the scores of the second and third principal components with the scores in respective positions being related to positions of measurement in the sample. As seen from FIG. 5(a) and FIG. 5(b), the relative levels of oxygenated hemoglobin and reduced hemoglobin as well as the blood total amount of a portion where a blood capillary is present was detected by the measuring apparatus of the invention.

Figure 6A:
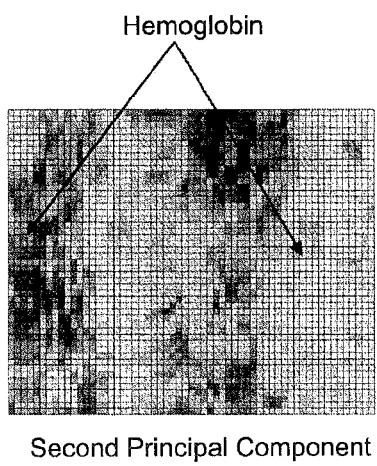
FIG. 6 is a two-dimensional representation of images of the score values from the normal skin measured by the apparatus of FIG. 1 with a wavelength band of from 500 nm to 850 nm according to the first embodiment of the invention.
Figure 6B:
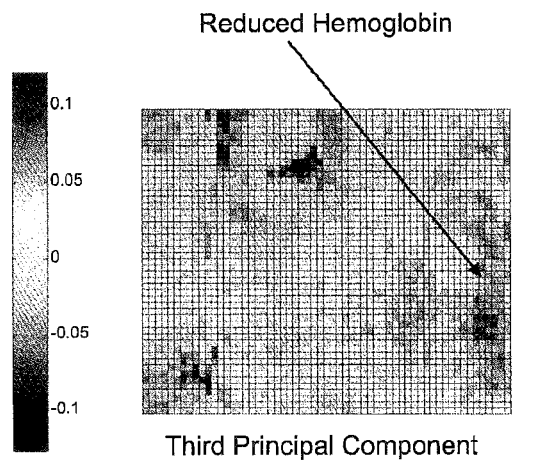

FIG. 6(a) and FIG. 6(b) also show the two-dimensional representation thereof as observed with a larger spectral region (i.e., from 500 nm to 850 nm). FIG. 6(a) shows the score of the second principal component, while FIG. 6(b) that of the third principal component. Like in FIG. 5, a portion where a blood capillary is present was detected.

For example, when circulation of the blood to the capillary vessel is sluggish such as in dialectical peripheral vascular obstruction syndrome, the eigenvector corresponding to the second principal component will take the form of the difference spectrum of oxygenated hemoglobin and reduced hemoglobin, and thus more reduced hemoglobin will be observed in a portion where the blood is stagnating (not shown).

Further, when the skin is successfully implanted after a skin transplant operation, then the blood will be flowing into the capillary vessel on the skin, so that the post-transplant condition of the skin can be sensed by detecting the presence of hemoglobin therein.

Figure 7:
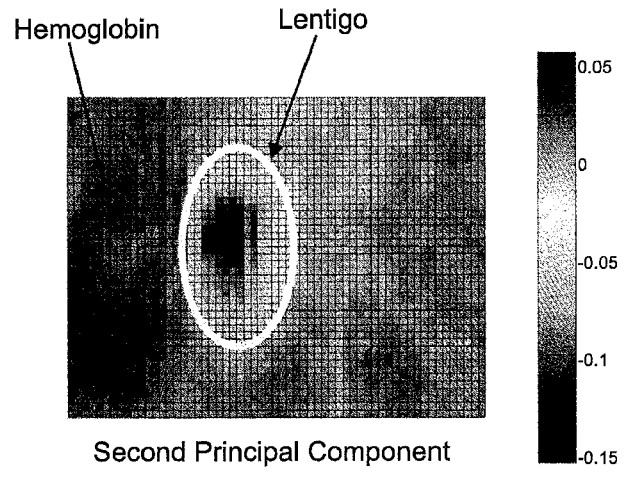
FIG. 7 is a two-dimensional representation of images of the score values of the second principal component from the skin including lentigo measured by the apparatus of FIG. 1 with a wavelength band of from 500 nm to 600 nm according to the second embodiment of the invention.
Figure 8:
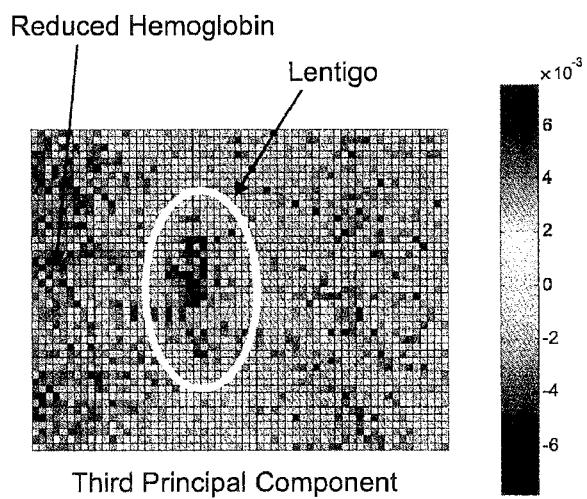
FIG. 8 is a two-dimensional representation of images of the score values of the third principal component from the skin including lentigo measured by the apparatus of FIG. 1 with a wavelength band of from 700 nm to 780 nm according to the second embodiment of the invention.

FIGS. 7 and 8 show a second embodiment where a portion including lentigo is measured. The result of measurement using a wavelength band from 500 nm to 600 nm is shown in FIG. 7, while the result of measurement using a wavelength band from 700 nm to 780 nm is shown in FIG. 8.

FIG. 7 is a two-dimensional representation of the score values of the second principal component with a wavelength band from 500 nm to 600 nm. As is seen therefrom, much hemoglobin is detected around the lentigo, while the lentigo portion strongly absorbs light and thus shows a low value.

FIG. 8 is a two-dimensional representation of the score values of the third principal component with a wavelength band from 700 nm to 780 nm. Reduced hemoglobin makes a large contribution to this component. FIG. 8 demonstrates that a lot of reduced hemoglobin is present around the lentigo.

For example, in some disease states, new blood vessels grow and concentrate around a tumor if there is a malignant melanoma so that hemoglobin around the tumor increases, and thus the image of the second principal component for a wavelength band from 500 nm to 600 nm is clearly different from that in the case of lentigo.

Moreover, due to a lot of oxygenated hemoglobin being present in new blood vessels, the score values of the images of the second and third principal components are clearly different from that in the case of lentigo, for a wavelength band from 700 nm to 780 nm.

Melanin (not shown) is one of the main components that are deposited in a skin surface layer to determine the color of the skin. Deposition of a large amount of melanin produces a spot or a lentigo. Since a portion with a lentigo has lots of melanin and light of a short wavelength is easy to be absorbed, light does not reach a dermis where blood vessels are present. Moreover, an absorption characteristic specific to melanin is also observed.

Although many researches on the melanin concentration using a spectroscopic method have been conducted since 1980s, they have remained in the discussions on chromatic coordinate parameter or melanin index, and have not yet reached concentration quantification.

Figure 9:
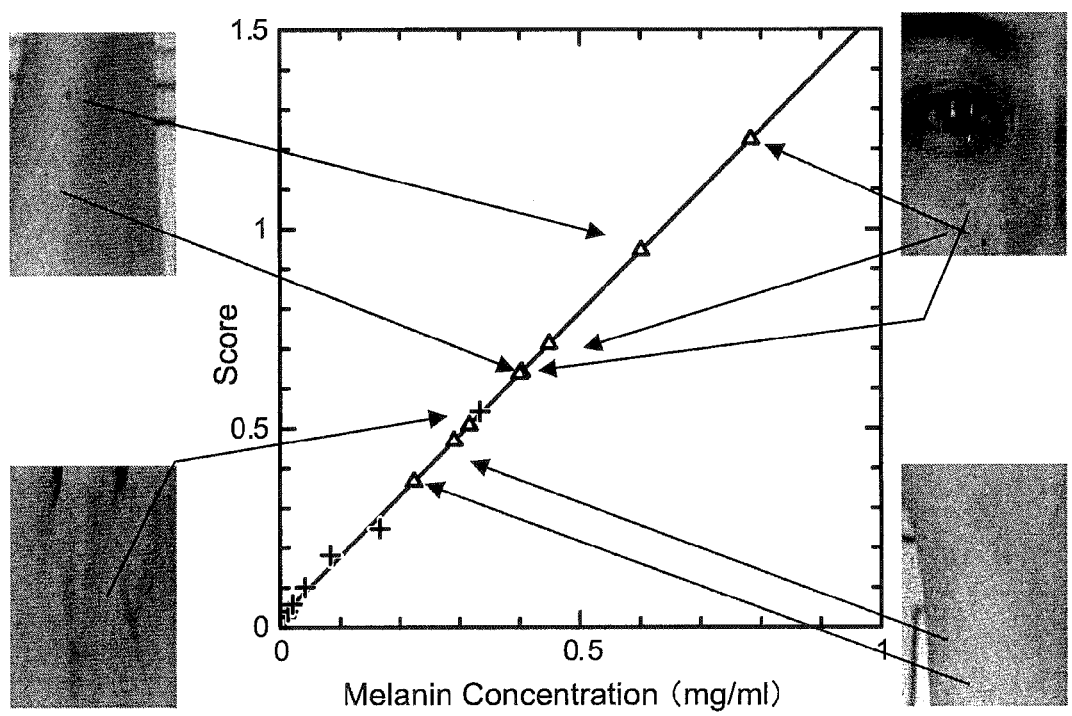
FIG. 9 is a graph showing relationship between a melanin concentration and a score in the direction of an eigenvector corresponding to melanin.

In order to measure the concentration of melanin, visible-range absorption spectrum from the skin was first analyzed using the technique of the multivariate analysis of the present invention, to thereby determine the eigenvector corresponding to melanin, while a calibration curve was drawn as shown in FIG. 9, using a skin model made of melanin and collagen.

By using this calibration curve, the melanin concentration in arbitrary portion can be predicted from the score value thereof.

Figure 10A:
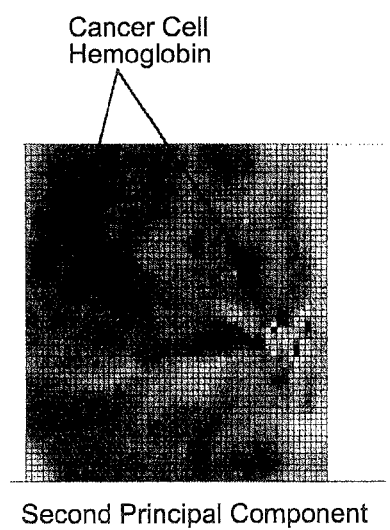
FIG. 10 is a two-dimensional representation of images of the score values from the skin having a cancer cell measured by the apparatus of FIG. 1 with a wavelength band of from 500 nm to 600 nm according to the third embodiment of the invention.
Figure 10B:
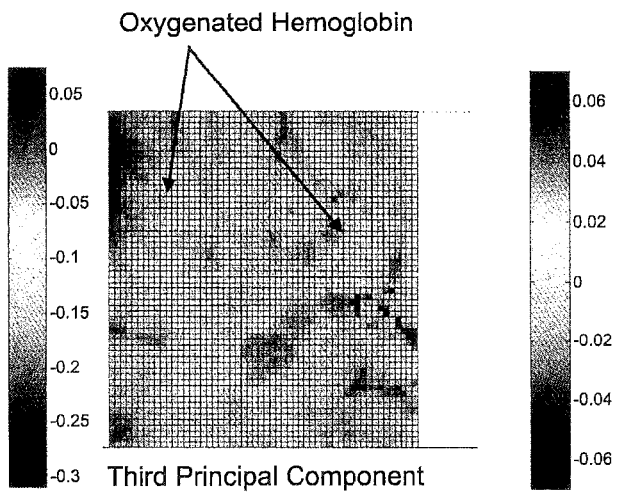

As for a third embodiment, the score of the second principal component when using a sample having a cancer cell and the wavelength band from 500 nm to 600 nm is shown in FIG. 10(a), while that of the third principal component is shown in FIG. 10(b). The score of the second principal component when using the wavelength band from 500 nm to 800 nm is shown in FIG. 11, while the score of the third principal component when using the wavelength band from 700 nm to 780 nm is shown in FIG. 12, respectively.

Figure 11:
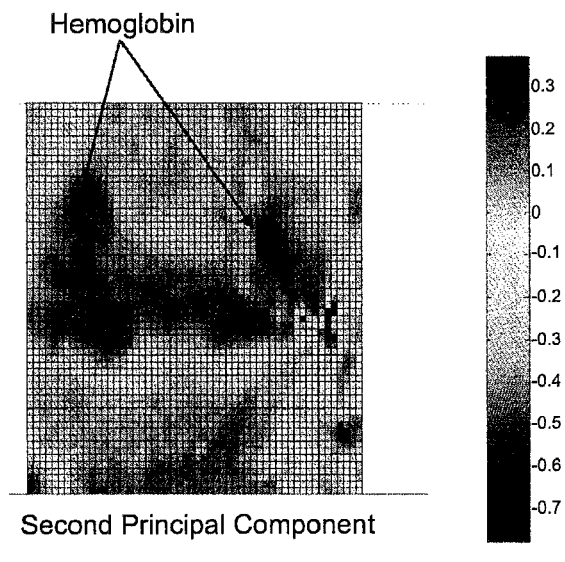
FIG. 11 is a two-dimensional representation of images of the score values from the skin having a cancer cell measured by the apparatus of FIG. 1 with a wavelength band of from 500 nm to 800 nm according to the third embodiment of the invention.
Figure 12:
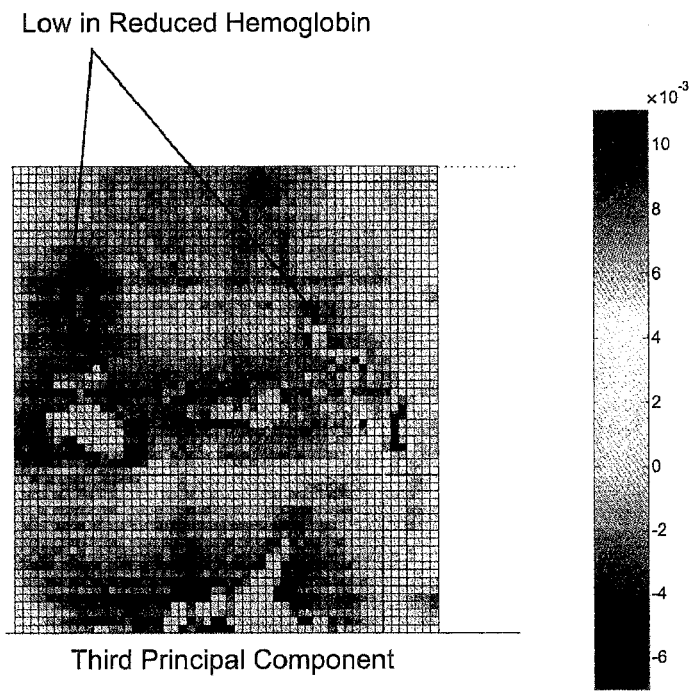
FIG. 12 is a two-dimensional representation of images of the score values from the skin having a cancer cell measured by the apparatus of FIG. 1 with a wavelength band of from 700 nm to 780 nm according to the third embodiment of the invention.

Since vascular growth occurs around a cancer cell and hence hemoglobin increases there, the score of the second principal component in the periphery of the cancer cell becomes large, as can be observed from FIG. 10(a) and FIG. 11.

Also, vascular growth occurs around a cancer cell and hence oxygenated hemoglobin increases while reduced hemoglobin decreases relatively. Accordingly, as shown in FIG. 10(b), comparatively a large amount of oxygenated hemoglobin was present around a cancer cell, and the score of the third principal component was high. Moreover, as shown in FIG. 12, it can be observed that the score of the third principal component in the case of using wavelength band from 700 nm to 780 nm decreased around a cancer cell.

As a fourth embodiment, one example is shown that verifies the therapeutic effect on cancer when using talaporfin as a light-sensitive substance. It is known that talaporfin as a light-sensitive substance is accumulated into a macrophage around a cancer cell, and that if a light of a certain wavelength (intrinsic absorption region) specifically absorbed by talaporfin is irradiated thereto, active oxygen is generated at the time of decomposition of talaporfin, thus killing a cancer cell while clogging a new blood vessel, thereby providing an effective medical treatment for cancer. This is called Photo Dynamic Therapy (PDT).

Figure 13:
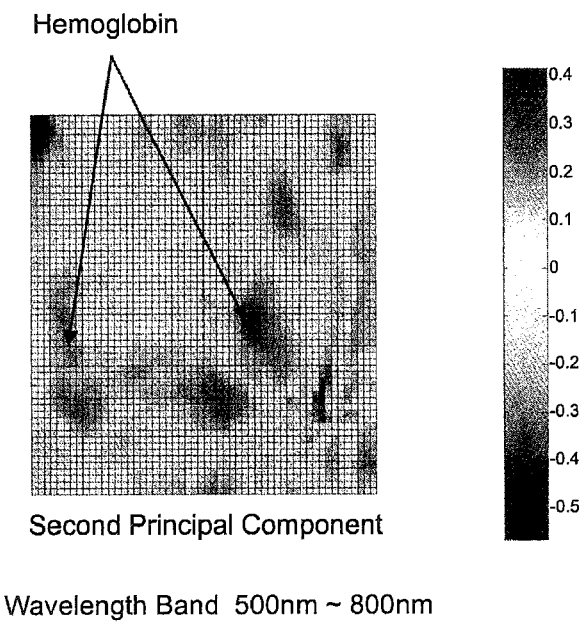
FIG. 13 a two-dimensional representation of images of the score values of the second principal component from the skin having a cancer cell after PDT treatment, measured by the apparatus of FIG. 1 with a wavelength band from 500 nm to 800 nm according to the fourth embodiment of the invention.
Figure 14:
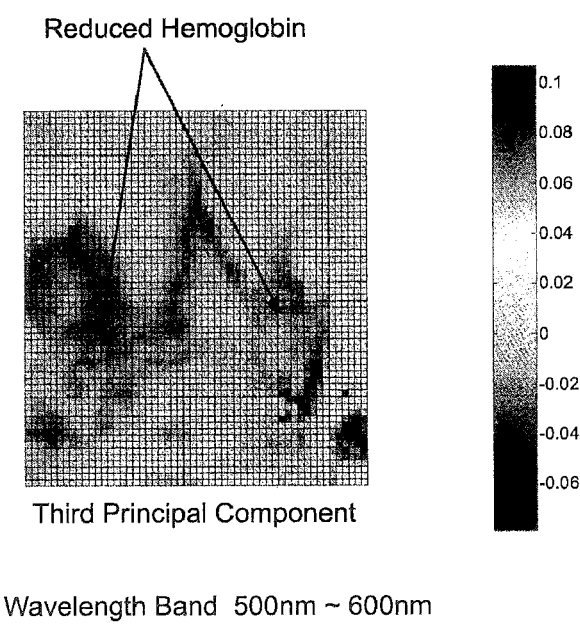
FIG. 14 a two-dimensional representation of images of the score values of the third principal component from the skin having a cancer cell after PDT treatment, measured by the apparatus of FIG. 1 with a wavelength band from 500 nm to 600 nm according to the fourth embodiment of the invention.

FIG. 13 shows the score of the second principal component for the wavelength band from 500 nm to 800 nm when the sample having a cancer cell of the third embodiment underwent the above-mentioned treatment, while FIG. 14 shows the score of the third principal component for the wavelength band from 500 nm to 600 nm, respectively.

As can be seen from FIGS. 13 and 14, it was demonstrated that hemoglobin was present around a cancer cell, and that it was rich in reduced hemoglobin. That is, it was demonstrated that the flow in oxygenated hemoglobin-rich new blood vessels was inhibited.

Figure 15:
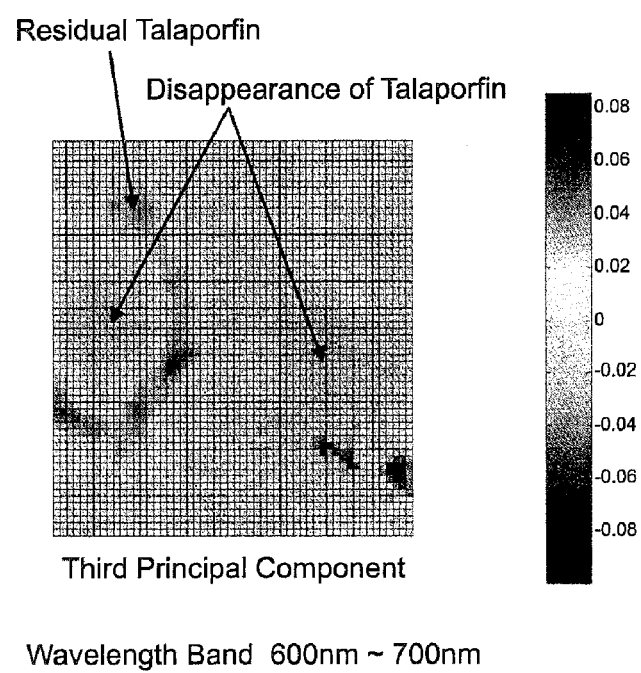
FIG. 15 a two-dimensional representation of images of the score values of the third principal component, measured by the apparatus of FIG. 1 with a wavelength band from 600 nm to 700 nm according to the fourth embodiment of the invention.

On the other hand, since the intrinsic absorption region of tissue-bonded talaporfin is in a range of from 660 nm to 670 nm (center wavelength: 664 nm), the result of analysis using a wavelength band including that wavelength is shown in FIG. 15. FIG. 15 is a diagram showing the score of the third principal component, with a wavelength band from 600 nm to 700 nm.

It can be observed from FIG. 15 that talaporfin disappeared in the cancer cell, but remained a little in the peripheral portion thereof.

From the result, not only the therapeutic effect on cancer can be confirmed, but also the completeness of the treatment to cause talaporfin remaining around the cancer cell to disappear can be confirmed.

FIG. 16 shows a change of quantity of talaporfin with time from the administration of talaporfin to post-PDT.

Since talaporfin has a characteristic absorption band at 664 nm, the feature of this characteristic absorption band will appear in the second principal component if principal component analysis is performed with a wavelength band from 600 nm to 700 nm.

If the spectrums in all the observing places are projected onto the direction of the second principal component, the value obtained will serve as an index of talaporfin concentration. FIG. 16 shows the change of the amount of talaporfin with time, using the magnitude of the index thereof.

The drawings indicate that on a color scale, the warmer (the colder) the color is, the more (the less) talaporfin is present. It can be seen that soon after the administration by intravenous injection, talaporfin is increasingly accumulated around a cancer cell over timer, due to its affinity for cancer.

Figure 16A:
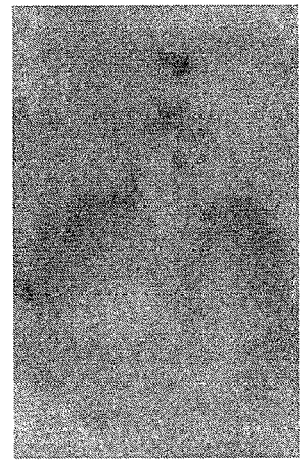
FIGS. 16a to 16f are diagrams showing the change of amount of talaporfin with time from the administration of talaporfin to post-PDT.
Figure 16B:
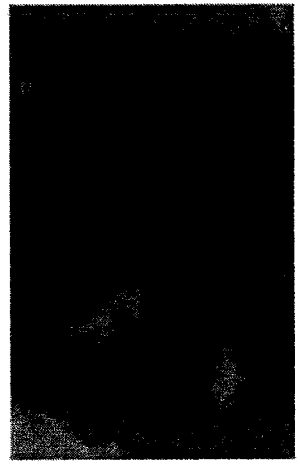
Figure 16C:
Figure 16D:
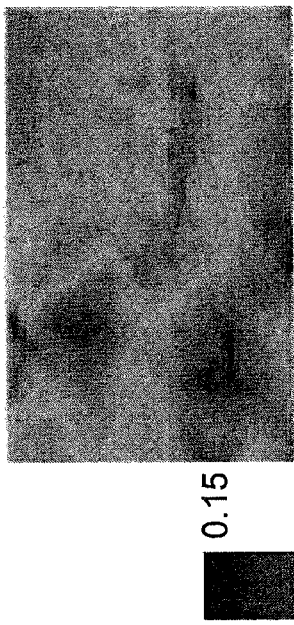
Figure 16E:
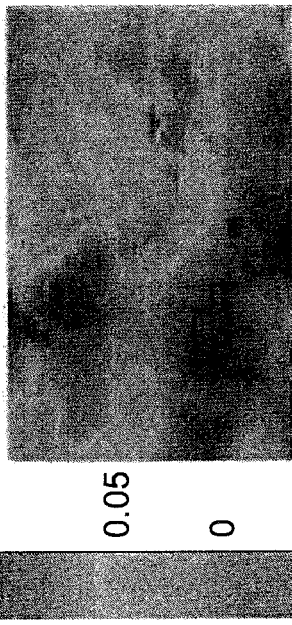
Figure 16F:
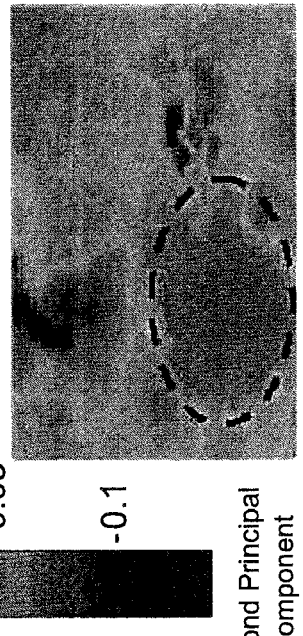
Figure 17A:
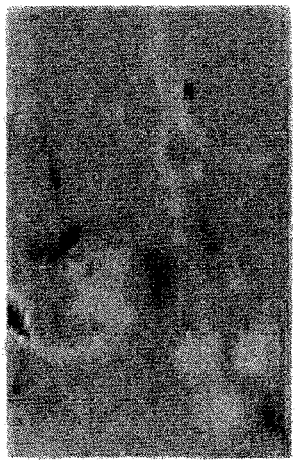
FIGS. 17a to 17f are diagrams showing the change of the score of the third principal component with time from the administration of talaporfin to post-PDT, with a wavelength band of from 500 nm to 600 nm.
Figure 17B:
Figure 17C:
Figure 17D:
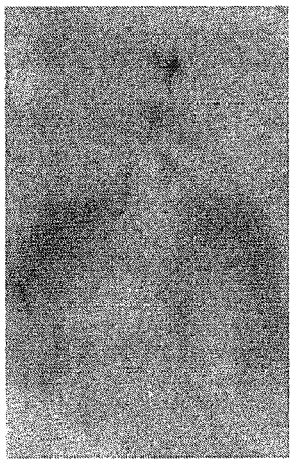
Figure 17E:
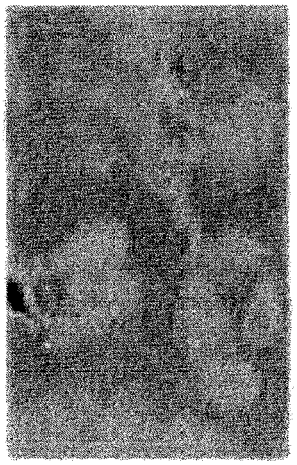
Figure 17F:

It is a well-known fact that after PDT (to a potion of cancer encircled by a dashed line in FIG. 16(f)) the tetrapyrrole ring of talaporfin is broken so that the 664 nm absorption peak disappears. It is to be noted that such fact is exactly reflected in FIG. 16(f).

When principal component analysis is performed with a wavelength band from 500 nm to 600 nm, the third principal component can be interpreted as a difference spectrum of an oxygenated hemoglobin spectrum and a reduced hemoglobin spectrum. Therefore, it follows that the larger (the smaller) the score of the third principal component is, the larger (smaller) amount of oxygenated (reduced) hemoglobin is relatively present.

FIG. 17 shows the change of the score of the third principal component with time. The drawings indicate that the warmer (the colder) the color is, the more oxygenated (reduced) hemoglobin is present. It can be seen that the vicinity of the cancer cell has more oxygenated hemoglobin as compared with the surrounding thereof.

This is in agreement with a clinical condition that the growth of new blood vessels occurs around a cancer cell. It is assumed that after PDT (to a potion of cancer encircled by a dashed line in FIG. 17(f)), blood vessels in the portion are clogged, so that the amount of reduced hemoglobin relatively increases around the cancer cell. It is to noted that such fact is exactly reflected in FIG. 17(f).

As a fifth embodiment, one example is shown that measures the amounts of hemoglobin and oxygenated hemoglobin in diagnosing the bloodstream on retina at the back of the eye. In the conventional diagnosis of the bloodstream on retina at the back of the eye, strong visible light is irradiated to the back of the eye to take an image thereof so as to make a diagnosis from the image, which, however, creates a painful burden to a test subject. Moreover, it often leads to erroneous diagnosis to make a diagnosis using a photograph of a surface only.

According to the method of the present invention, the two-dimensional display according to the blood flow of the fundus of the eye is obtained, and thus it is possible to observe where the test subject has an abnormality and how serious it is. Since visible light is too strong to open an eye, the present invention features the use of an eye-safe light of a near-infrared region of 700 nm or above. The scores of the second and third principal components are used for imaging, like the foregoing examples.

As a sixth embodiment, one example is shown that detects blood fluidity failure that causes organ microcirculation failure in the multiple risk-factor syndrome essentially consisting of hyperlipemia, abnormal glucose tolerance, obesity, insulin resistance syndrome, etc., through the analysis of change of the score of the second principal component with time.

The measurement is performed in such a manner that a part of a test subject's body such as his/her upper arm is compressed by a tourniquet to temporarily stop the flow of blood, and then loosen the tourniquet to thereby measure moment-to-moment change of the score of the principal component having an eigenvector indicative of a spectrum showing total amount of hemoglobin or a difference spectrum of oxygenated hemoglobin and reduced hemoglobin.

For example, in the wavelength band of 500 nm to 600 nm, the score of the second principal component indicates a relative amount of oxygenated hemoglobin and reduced hemoglobin, and thus the score takes a negative value when the flow of blood is temporarily stopped by the compression.

When the tourniquet is loosened, then the blood will flow out and the total amount of hemoglobin and the relative amount of oxygenated hemoglobin will increase. At that moment, if there is no blood fluidity failure, blood flow volume will be recovered promptly, but if there is, it will take time, thus making it possible to detect the presence of absence of failure.

Figures 18, 19:
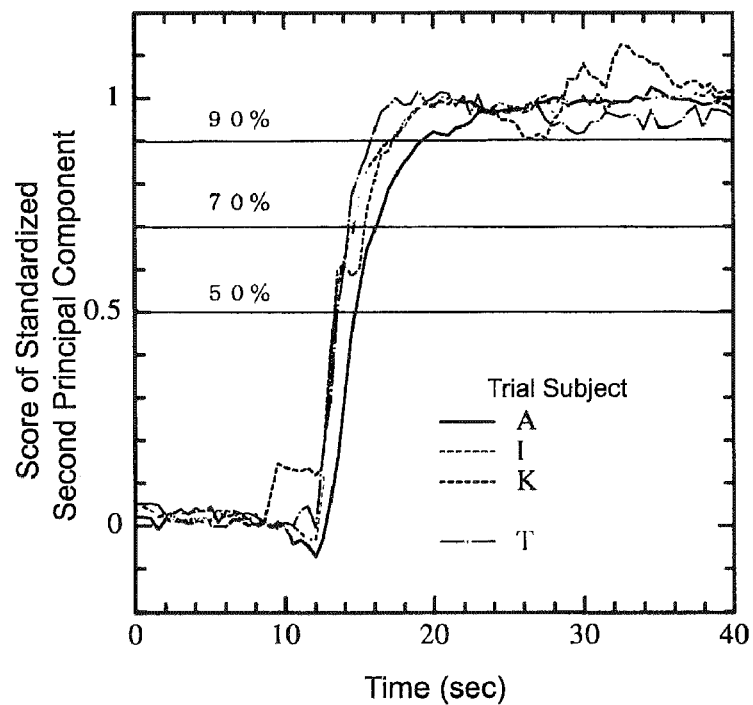
FIG. 18 is a graph showing the change of the score of the second principal component with time measured by the apparatus of FIG. 1 with a wavelength band from 500 nm to 600 nm according to the sixth embodiment of the invention.
FIG. 19 is a table showing the time taken for the score of the second principal component measured by the apparatus of FIG. 1 with a wavelength band from 500 nm to 600 nm to rise to 50%, 70% and 90%.

FIG. 18 shows a moment-to-moment change of the score of the second principal component with respect to five test subjects, using a wavelength band of 500 nm to 600 nm. The graph of FIG. 18 is standardized so that the score of the second principal component may vary between 0 and 1.

FIG. 19 shows the time taken for the standardized score of the second principal component to rise to 50%, 70% and 90%. Test subject A is a type II diabetic (fasting glucose level: 200 mg/dl), while the others are normal subjects (fasting glucose level: 95 mg/dl). It can be seen therefrom that the test subject A has a 90% rise time longer than the others.

FIG. 20 shows the time obtained from a moment-to-moment change of the score of the second principal component, in the wavelength band of 500 nm to 850 nm, using the same method as the above-mentioned. As can be also seen therefrom, the test subject A has a 90% rise time greater than the others. Thus way, blood fluidity failure can be easily detected through the observation of the moment-to-moment change of the score of the second principal component.

Moreover, since oxygenated hemoglobin will begin to flow into capillary vessels if the skin begins to be successfully implanted after a skin transplant operation, moment-to-moment change of the skin implantation condition can be known by observing change of the score of the second principal component over time, using the same method as the above-mentioned method.

The present invention shall not be limited to the foregoing embodiments, but various changes and modifications should be construed as being included therein if such changes and modifications can achieve effects equivalent to those of the present invention, and are made by one skilled in the art, based on substantially the same idea as the present invention.

The invention claimed is:

1. A measuring method comprising the steps of:
    irradiating a white light to a biological surface as a sample;
    detecting a spectrum of the white light reflected from two or more positions on said biological surface;
    plotting an absorbance of said spectrum to a spectral multi-dimensional space of light;
    conducting a multivariate analysis of a data on said spectral multi-dimensional space obtained from said two or more positions to obtain eigenvectors of at least first, second and third principal components; and
    projecting the data of each position onto a direction of the eigenvector of said at least three principal components to measure at least one of a total amount of hemoglobin, an amount of melanin, an amount of talaporfin, and a difference in amount between oxygenated hemoglobin and reduced hemoglobin, which exist on said biological surface, based on a magnitude of the component of said data with respect to the direction of said eigenvector.

2. The method according to claim 1, wherein said multivariate analysis is conducted with said spectrum of light having wavelength bands of from 500 to 600 nm and 500 to 850 nm.

3. The method according to claim 1, wherein said multivariate analysis is conducted with said spectrum of light having wavelength bands of from 500 to 600 nm and 700 to 780 nm.

4. The method according to claim 1, wherein said multivariate analysis is conducted with said spectrum of light having wavelength bands of from 500 to 600 nm, 500 to 850 nm and 700 to 780 nm.

5. The method according to claim 1, wherein talaporfin is administered to said biological surface so that said multivariate analysis is conducted with said spectrum of light having a basic wavelength band of from 600 to 700 nm.

6. The method according to claim 1, wherein said multivariate analysis is conducted with said spectrum of light having a basic wavelength band of 700 nm or above.

7. The method according to claim 1, wherein said multivariate analysis is conducted with said spectrum of light having basic wavelength bands of from 500 to 600 nm and 500 to 850 nm, while a data of at least one position on said biological surface is projected onto the directions of the eigenvectors of said second and third principal components to display a change of magnitude thereof with time.

8. An apparatus for measuring comprising:
    an irradiating device configured for irradiating a white light to a biological surface as a sample;
    a detector configured for detecting a spectrum of the white light reflected from two or more positions on said biological surface;
    a plotter plotting an absorbance of said spectrum to a spectral multi-dimensional space of light;
    a calculator obtaining eigenvectors of at least first, second and third principal components by conducting a multivariate analysis of data on said spectral multi-dimensional space obtained from said two or more positions and measuring at least one of a total amount of hemoglobin, an amount of melanin, an amount of talaprofin, and a difference in amount between oxygenated hemoglobin and reduced hemoglobin, which exist on said biological surface; and a display displaying a magnitude of the component of said data on a gray scale or in colors according to the magnitude, on a two-dimensional screen by projecting the data of each position onto a direction of the eigenvector of said at least three principal components, based on the magnitude of the component of said data with respect to the direction of said eigenvector.

9. The apparatus according to claim 8, wherein said irradiating device is provided integrally with a condenser condensing reflection from two or more positions on said biological surface by combining them with an optical fiber.

* * * * *